(12) United States Patent
Reven et al.

(10) Patent No.: US 8,053,444 B2
(45) Date of Patent: Nov. 8, 2011

(54) SIROLIMUS FORMULATION

(75) Inventors: Sebastjan Reven, Jesenice (SI); Igor Legen, Grosuplje (SI); Zdenka Jerala-Strukelj, Mavcice (SI)

(73) Assignee: Lek Pharmaceuticals d.d., Ljubljana (SI)

( * ) Notice: Subject to any disclaimer, the term of this patent is extended or adjusted under 35 U.S.C. 154(b) by 111 days.

(21) Appl. No.: 12/011,072

(22) Filed: Jan. 24, 2008

(65) Prior Publication Data

US 2008/0176888 A1      Jul. 24, 2008

(30) Foreign Application Priority Data

Jan. 24, 2007   (EP) ..................................... 07101079

(51) Int. Cl.
*A61K 31/436* (2006.01)
(52) U.S. Cl. ...................................................... 514/291
(58) Field of Classification Search .................... 514/291
See application file for complete search history.

(56) References Cited

U.S. PATENT DOCUMENTS

| | | | |
|---|---|---|---|
| 3,929,992 A | 12/1975 | Sehgal et al. | |
| 2003/0180352 A1* | 9/2003 | Patel et al. | 424/465 |
| 2003/0211160 A1 | 11/2003 | Guitard et al. | |

FOREIGN PATENT DOCUMENTS

| | | |
|---|---|---|
| EP | 0868911 A2 | 10/1998 |
| EP | 1092429 A1 | 4/2001 |
| WO | WO2006/039237 A1 * | 4/2006 |
| WO | WO2006/094507 | 9/2006 |

OTHER PUBLICATIONS

Morissette et al. (Advanced Drug Delivery Reviews, vol. 56, pp. 275-300; 2004).*
Vippagunta et al. (Advanced Drug Delivery Reviews, vol. 48, Abstract; 2001).*

* cited by examiner

*Primary Examiner* — Jeffrey S Lundgren
*Assistant Examiner* — Nelson Blakely, III
(74) *Attorney, Agent, or Firm* — Luedeka, Neely & Graham, P.C.

(57) ABSTRACT

The present invention relates to a stable pharmaceutical composition that includes sirolimus. The pharmaceutical composition includes sirolimus in the amorphous form, a fatty acid ester, such as glyceryl behenate, and a pharmaceutically acceptable polymer wherein the fatty acid ester is present at a concentration of less than 10% w/w compared to the total weight of the composition.

7 Claims, No Drawings

SIROLIMUS FORMULATION

This application claims the benefit of foreign application No. EP07101079.7 filed Jan. 24, 2007, which is hereby incorporated herein by reference.

FIELD OF THE INVENTION

The present invention relates to a stable pharmaceutical composition comprising sirolimus.

BACKGROUND OF THE INVENTION

Sirolimus (offered commercially by Wyeth as RAPAMUNE) is a macrocyclic lactone produced by *Streptomyces hygroscopicus* used for immunosuppression following renal transplantation. The chemical name of sirolimus (also known as rapamycin) is (3S,6R,7E,9R,10R,12R,14S,15E,17E,19E, 21S,23S,26R,27R,34aS)-9,10,12,13, -14,21,22,23,24,25,26, 27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethox-y-6,8,12,14,20,26-hexamethyl-23,27-epoxy-3H-pyrido[2,1-c][1,4]oxaazacycloh-entriacontine-1,5,11,28,29(4H,6H,31H)-pentone. The molecular formula thereof is $C_{51}H_{79}NO_{13}$ and the molecular weight is 914.2. The structural formula of sirolimus is shown below:

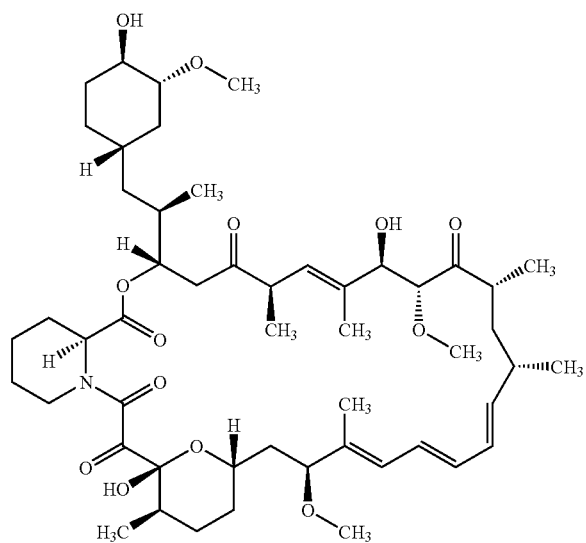

The commercially available product containing sirolimus is RAPAMUNE. Sirolimus inhibits T lymphocyte activation and proliferation that occurs in response to antigenic and cytokine (Interleukin [IL]-2, IL-4, and IL-15) stimulation; it also inhibits antibody production. In cells, sirolimus binds to the immunophilin, FK Binding Protein-12 (FKBP-12), to generate an immunosuppressive complex. This complex binds to and inhibits the activation of the mammalian Target Of Rapamycin (mTOR), a key regulatory kinase. This inhibition suppresses cytokine-driven T-cell proliferation, inhibiting the progression from the G1 to the S phase of the cell cycle. In rodent models of autoimmune disease, sirolimus suppresses immune-mediated events associated with systemic lupus erythematosus, collagen-induced arthritis, autoimmune type I diabetes, autoimmune myocarditis, experimental allergic encephalomyelitis, graft-versus-host disease, and autoimmune uveoretinitis.

Sirolimus is a white to off-white powder and is insoluble in water, but freely soluble in benzyl alcohol, chloroform, acetone, and acetonitrile. Sirolimus is characterized in that it has a very low solubility in water (only 2.6 µg/ml); therefore only about 0.65 mg of sirolimus is dissolved in a volume of 250 ml of gastrointestinal fluid which is not enough to cause therapeutic effect. To ensure that all sirolimus from the oral dosage form is dissolved in the gastrointestinal fluid, sirolimus is available as an oral solution containing 1 mg/ml of sirolimus and as tablet containing 1 mg or 2 mg of nanosized (less than 400 nm) particles of sirolimus. However preparation of an oral solution of sirolimus before administration requires a special procedure and is thus less preferable from the patient's point of view. Sirolimus in the form of a solid dispersion is described in WO 97/03654. Preparation of tablets containing nanosized particles of sirolimus is described in U.S. Pat. No. 5,989,591. The preparation of nanosized particles of sirolimus and the preparation of sirolimus tablets containing nanosized particles of sirolimus are both complex procedures and may result in batch-to-batch variations in the dissolution of sirolimus from the tablets. Therefore an alternative approach for the enhancement of sirolimus solubility is desirable. Sirolimus is available in the form of crystalline powder. It is known to a skilled person that the transformation of the crystalline form of a low solubility drug to the amorphous form can significantly increase the solubility thereof, which is also true for sirolimus. However amorphous sirolimus is extremely chemically unstable and is therefore not easily acceptable for the incorporation into an oral pharmaceutical dosage form. Pharmaceutical dosage forms comprising amorphous sirolimus are described in WO 06/039237 and WO 06/094507. In WO 06/094507, a modified release pharmaceutical formulation comprising sirolimus and glyceryl monostearate at a concentration of 49.25% is described. The release rate of sirolimus from the delayed release rate formulations disclosed in WO 06/094507 is significantly suppressed compared to the marketed sirolimus formulation (RAPAMUNE).

The present invention is aimed at mitigating the problems described above. It relates to a stable pharmaceutical formulation in a solid dosage form for oral administration with enhanced dissolution properties of sirolimus.

SUMMARY OF INVENTION

The present invention employs an ester and a polymer in a pharmaceutical composition comprising sirolimus. The concentration of the ester is less than 10% of the total weight of the composition. In this way, the stability of sirolimus in the composition is increased and the release rate is not adversely affected.

In the first aspect, the invention relates to a pharmaceutical composition comprising sirolimus in the amorphous form, a fatty acid ester and a pharmaceutically acceptable polymer wherein the fatty acid ester is present at a concentration of less than 10% w/w of the total weight of the composition.

In another aspect, the invention relates to a pharmaceutical composition comprising sirolimus in the amorphous form, a fatty acid ester, formed from a basic molecule: with formula $C_xH_yO_z$, wherein x=1-3, y=1-10 and z=1-3, esterified with a saturated or an unsaturated fatty acid, and a pharmaceutically acceptable polymer wherein the fatty acid ester is present at a concentration of less than 10% w/w of the total weight of the composition.

In another aspect, the invention relates to a use of such pharmaceutical compositions comprising sirolimus in the amorphous form for immunosuppression following renal transplantation or other related conditions or diseases.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The present invention relates to a pharmaceutical composition comprising sirolimus in the amorphous form, a fatty acid ester and a pharmaceutically acceptable polymer wherein the fatty acid ester is present at a concentration of less than 10% w/w based the total weight of the composition.

Sirolimus present in the composition of the invention is in the amorphous form. Thus the pharmaceutical composition is preferably in a solid dosage form.

Sirolimus according to the invention may be sirolimus per se or any sirolimus derivative or analogue. Sirolimus derivatives are well known in the art and include, for example 32-deoxosirolimus, 16-pent-2-ynyloxy-32-(S)-dihydrosirolimus, 16-O-substituted sirolimus, 26-O-substituted sirolimus, 28-O-substituted sirolimus, 32-O-substituted sirolimus, 40-O-substituted sirolimus, ester derivatives and others. For example, the derivative may be an O-substituted derivative in which the hydroxyl group on the cyclohexyl ring of sirolimus is replaced by —$OR_1$, in which $R_1$ is hydroxyalkyl, hydroxyalkoxyalkyl, acylaminoalkyl and aminoalkyl; for example, 40-O-(2-hydroxy)ethyl-sirolimus, 40-O-(3-hydroxy)propyl-sirolimus, 40-O-[2-(2-hydroxy)ethoxy]ethyl-sirolimus or 40-O-(2-acetaminoethyl)-sirolimus. Other sirolimus derivatives may also be used.

The fatty acid ester may be formed from any fatty acid, for example a saturated, an unsaturated or a branched chain fatty acid. Examples of fatty acids include but are not limited to caprylic acid, capric acid, lauric acid, linoleic acid, myristic acid, palmitic acid, stearic acid, oleic acid or behenic acid.

The fatty acid ester used in the composition may be a fatty acid ester formed from a basic molecule with formula $C_xH_yO_z$, wherein x=1-3, y=1-10 and z=1-3).

The fatty acid ester used in the composition may be a fatty acid ester with an alcohol, such as an ester of a monohydric alcohol or a polyhydric alcohol, a sorbitan fatty acid ester or a sugar fatty acid ester such as sucrose ester.

In one embodiment, the composition comprises a glycerol fatty acid ester, i.e. a glyceride. For example, the ester may be a substituted or unsubstituted mono-, di-, or triglyceride. Glycerol esters of fatty acids include mono-, di-, or triglycerol with behenic acid or lactic acid, citric acid, succinic acid, tartaric acid, acetic acid or ricinoleic acid.

In one embodiment, the glycerol fatty acid ester is glyceryl behenate. Other examples include glycerol monostearate or glycerol palmitostearate.

The addition of a fatty pharmaceutical excipient, such as an ester of glycerol with a fatty acid, into the pharmaceutical dosage form containing sirolimus in the form of a solid solution can improve the stability of sirolimus. The concentration of the ester of glycerol with a fatty acid in the formulation is less than 10% w/w of the total composition, as at such concentration no suppressing effect on the release rate of active pharmaceutical ingredient from the pharmaceutical formulation is obtained. If the glycerol ester is present at a concentration which is higher than 10% w/w of the total composition, then it suppresses the release rate of sirolimus from the formulation. This can lead to insufficient absorption from the gastrointestinal tract. A preferred concentration of the glycerol ester is 1 to 5% or 5 to 9%.

The composition also includes pharmaceutically acceptable polymers. These can be used to increase the stability of the composition. Suitable polymers include polyvinylpyrrolidone (PVP), hydroxypropylcellulose (HPC) or hydroxypropylmethylcellulose (HPMC). The polymer may be present in an amount of 1 to 20% w/w of the total tablet weight. The preferred polymer is hydroxypropylcellulose (HPC).

Compositions of this invention may be administered in any convenient solid dosage form, for example as a tablet, capsule, granule or powder form, e.g. in a sachet.

The dosage form used, e.g. a tablet, may be coated, for example using a conventional film coating or an enteric coating. Suitable coatings may comprise hydroxypropylmethylcellulose for a conventional film coating or cellulose acetate phthalate; hydroxypropylmethylcellulose phthalate; a polymethyacrylic acid copolymer, e.g. Eudragit L or S; or hydroxypropylmethylcellulose acetate succinate for an enteric coating. Sirolimus may be present in the composition in an amount of about 0.01 to about 30% w/w based on the weight of the composition (% w/w), and preferably in an amount of 0.1 to 20% w/w based on the total weight of the composition.

The composition may further comprise a polyethylene glycol (PEG). Examples include PEGs having the average molecular weight between 1000 and 9000 Daltons, e.g. between about 1800 and 7000, for example PEG 2000, PEG 4000 or PEG 6000. Also included may be a cyclodextrin, for example a β-cyclodextrin or an α-cyclodextrin. Examples of suitable β-cyclodextrins include methyl-β-cyclodextrin; dimethyl-β-cyclodextrin; hydroxypropyl-β-cyclodextrin; glycosyl-β-cyclodextrin; maltosyl-β-cyclodextrin; sulfo-β-cyclodextrin; sulfo-alkylethers of β-cyclodextrin, e.g. sulfo-$C_{1-4}$-alkyl ethers. Examples of α-cyclodextrins include glucosyl-α-cyclodextrin and maltosyl-α-cyclodextrin.

The composition may further comprise a water-soluble or water-insoluble saccharose or another acceptable carrier or filler such as lactose, or microcrystalline cellulose. One or more surfactants, antioxidants and/or stabilizers may also be included.

The invention will be further understood with references to the non-limiting examples.

EXAMPLES

Solid solutions of sirolimus were prepared by evaporating ethanol from an ethanolic solution of sirolimus in the presence of stabilizing pharmaceutical excipients which may be dissolved or suspended in the ethanolic sirolimus solution. The origination of a solid solution of sirolimus was checked by X-ray diffraction analysis and Raman microscopy. Pure amorphous sirolimus was prepared in Example 1 and a number of pharmaceutical compositions comprising sirolimus were prepared in examples 2 to 6 below. These were exposed then to stress stability testing at 60° C. for 14 days and at 40° C. and 75% relative humidity for one month in vials. The amount of degradation products formed was compared to the samples of commercially available tablets comprising sirolimus.

Example 1

A saturated solution of sirolimus in a mixture of water and tert-butanol (70/30 v/v) was prepared. The solution was frozen in the presence of liquid nitrogen and subjected to lyophilisation under reduced pressure and at room temperature. The amorphous form of sirolimus was confirmed by X-ray diffraction.

Example 2

1 gram of sirolimus and 3 grams of povidone were dissolved in 15 grams of ethanol (96%). The prepared solution was dispersed on pregelatinized starch to obtain granular material. Granulation was carried out in a fluid-bed dryer. The dry granules were then sieved and compressed into cores. The amorphous form of sirolimus was confirmed by X-ray diffraction.

Example 3

1 gram of sirolimus and 3 grams of hydroxypropyl cellulose (Klucel EF) were dissolved in 40 grams of ethanol (96%). The prepared solution was dispersed on pregelatinized starch to obtain granular material. Granulation was carried out in a fluid-bed dryer. The dry granules were then sieved and compressed into cores. The amorphous form of sirolimus was confirmed by X-ray diffraction.

Example 4

1 gram of sirolimus was dissolved in 20 grams of ethanol (96%) and mixed with 5 grams of low substituted hydroxypropylcellulose (L-HPC 20). Ethanol was evaporated under the normal pressure at 30° C. The amorphous form of sirolimus was confirmed by X-ray diffraction.

Example 5

1 gram of sirolimus and 3 grams of hydroxypropyl cellulose (Klucel EF) were dissolved in 40 grams of ethanol (96%). The prepared solution was dispersed on pregelatinized starch to obtain granular material. Granulation was carried out in a fluid-bed dryer. The dry granules were then sieved and glyceryl behenate was added. Cores with the weight of 306 mg were compressed on a rotary compressing machine.

TABLE 1

| Composition of Example 5. | |
| --- | --- |
| Core | w/w % |
| Sirolimus | 0.65 |
| Hydroxypropyl cellulose | 1.96 |
| Starch pregelatinized | 47.39 |
| Glyceryl behenate | 50.00 |

The amorphous form of sirolimus was confirmed by X-ray diffraction.

Example 6

1 gram of sirolimus, 0.75 g of colloidal anhydrous silica, and 5 grams of hydroxypropyl cellulose. (Klucel EF) were dissolved in 60 grams of ethanol (96%). The prepared solution was dispersed on pregelatinized starch to obtain granular material. Granulation was carried out in a fluid-bed dryer. The dry granules were then sieved and 6 g of glyceryl behenate and 17.25 g of silicified microcrystalline cellulose were added. Cores with the weight of 300 mg were compressed on a rotary compressing machine. Tablets were film coated with a coloured suspension. The ingredients of the film coating do not modify the release rate of sirolimus. The amorphous form of sirolimus was confirmed by X-ray diffraction. The percentage in w/w % of the various components is shown in Table 2:

TABLE 2

| Composition of Example 6. | |
| --- | --- |
| | % |
| Core | |
| Sirolimus | 0.65 |
| Hydroxypropyl cellulose | 3.25 |
| Colloidal silicon dioxide | 0.50 |
| Starch pregelatinized | 77.92 |
| Glyceryl behenate | 3.90 |
| Silicified microcrystalline cellulose | 11.20 |
| Film coat | |
| Hydroxypropyl methylcellulose - Pharmacoat | 1.30 |
| Hydroxypropyl cellulose - Klucel | 0.32 |
| Polyethylene glycol 400 | 0.32 |
| Titanium dioxide E 171 | 0.42 |
| Pigment-iron oxide E 172 | 0.06 |
| Talc | 0.16 |
| Total weight | 100.00% |

TABLE 3

| Results of stability tests | | | |
| --- | --- | --- | --- |
| Example no. | Time of testing/ Testing condition | Total sum of impurities | Max.unknown impurity |
| Substance in a crystal form | 0 | 0.70 | 0.19 |
| | 14 days, 60° C. | 0.60 | 0.26 |
| | 1 month, 40° C./75% | 0.59 | 0.26 |
| Example 1 | 0 | 3.34 | 0.25 |
| | 7 days, 60° C. | 9.09 | 1.91 |
| Example 2 | 0 | 1.85 | 1.06 |
| | 14 days, 60° C. | 6.24 | 2.26 |
| | 1 month, 40° C./75% | 3.56 | 1.84 |
| Example 3 | 0 | 0.73 | 0.24 |
| | 14 days, 60° C. | 3.56 | 1.11 |
| | 1 month, 40° C./75% | 2.40 | 0.73 |
| Example 4 | 0 | 0.93 | 0.48 |
| | 14 days, 60° C. | 4.84 | 0.87 |
| | 1 month, 40° C./75% | 1.63 | 0.56 |
| Example 5 | 0 | / | / |
| | 14 days, 60° C. | 3.96 | 0.38 |
| | 1 month, 40° C./75% | 1.20 | 0.31 |
| Example 6 | 0 | / | / |
| | 14 days, 60° C. | 3.38 | 0.95 |
| | 1 month, 40° C./75% | 0.97 | 0.28 |
| Rapamune ® 2 mg | 0 | 0.58 | 0.13 |
| | 14 days, 60° C. | 6.68 | 4.36 |
| | 1 month, 40° C./75% | 1.95 | 0.59 |

The HPLC analyses were performed with a Waters system equipped with a Synergi Max-RP, 5 μm, 250×4.6 mm column which was maintained in a column oven at 40° C. The mobile phase consisted of a 40:54:6 (V/V/V) mixture of $CF_3COOH$/NaOH with pH 2.5, acetonitrile and water. The flow rate was 1.4 mL/min, and the detection wavelength was 278 nm. All impurities eluted within 70 minutes represent the total amount of sirolimus impurities.

It is generally recognized that for most drug degradation, the reaction rate of the solid-state degradation is increased when the crystalline form of the drug is rendered partially or fully amorphous (substance in a crystalline form/amorphous substance).

One can see that the sirolimus in the amorphous form, prepared according to Example 1, is significantly less stable compared to the substance in the crystalline form.

However the stability of amorphous sirolimus can be increased by forming a solid solution of sirolimus in a pharmaceutically acceptable polymer and additionally with the inclusion of a fatty acid ester to this solid solution.

For the stability studies, two solid solutions were prepared using ethanol-soluble polymers polyvinylpyrrolidone (PVP) or hydroxypropylcellulose (HPC). The chemical stability was monitored for 14 days at 60° C. and 1 month at 40° C. and 75% relative humidity. The samples were stored in vials. Both polymers proved to enhance the stability of the amorphous sirolimus (Example 1 compared to Example 2 and Example 3); however HPC proved to be more effective (Example 2 compared to Example 3).

Further studies demonstrated that not only ethanol soluble carriers are able to enhance the stability of amorphous sirolimus. A stable amorphous sirolimus preparation was prepared by evaporating ethanol from the ethanolic solution of sirolimus in the presence of a low substituted hydroxypropylcellulose, which was suspended in the ethanolic sirolimus solution (Example 4). The results are summarized in the table 3 above and clearly demonstrate that the stability of amorphous sirolimus was significantly improved (Example 1 compared to Example 4).

Most surprisingly it can be seen that the addition of a fatty pharmaceutical excipient, such as an ester of glycerol with a fatty acid, into the pharmaceutical composition comprising the amorphous sirolimus additionally reduces the degradation of sirolimus (see Example 3 compared to Example 6).

A stable pharmaceutical formulation comprising the amorphous sirolimus was prepared according to Example 6. The stability of this formulation is superior regarding the chemical stability of sirolimus compared to commercially available sirolimus product (RAPAMUNE).

In conclusion, it can be seen from Example 6 that the inclusion of both a polymer and a fatty acid ester at a low concentration of the fatty acid ester results in significantly improved stabilisation of the amorphous sirolimus. The increase in stability of the composition comprising a polymer and a fatty acid ester at a low concentration (Example 6) of the fatty acid ester is greater than when the fatty ester is present at a high concentration (as in Example 5). In addition, it is advantageous that the fatty acid ester is present at a low concentration, because in that case it does not substantially affect the release rate of sirolimus.

The invention claimed is:

1. A pharmaceutical composition comprising a tablet core which comprises sirolimus in the amorphous form; a fatty acid ester comprising glyceryl behenate; and a pharmaceutically acceptable polymer wherein said fatty acid ester is present at a concentration of less than 10% w/w of the total weight of the composition.

2. The pharmaceutical composition according to claim 1, wherein said pharmaceutical composition is in a solid dosage form.

3. The pharmaceutical composition according to claim 2, in a tablet form further comprising a conventional film coating or an enteric coating on the surface of the tablets.

4. The pharmaceutical composition according to claim 1, wherein said polymer is a pharmaceutically acceptable polymer selected from the group consisting of HPC, HPMC and PVP.

5. The pharmaceutical composition according to claim 1, wherein said polymer is present at a ratio of 1 to 20% w/w of the total weight of a solid dosage form.

6. The pharmaceutical composition according to claim 1, wherein the concentration of said fatty acid ester is from 1 to 5% w/w based on the total weight of the composition.

7. The pharmaceutical composition according to claim 1, formulated as a tablet or capsule.

* * * * *

UNITED STATES PATENT AND TRADEMARK OFFICE
CERTIFICATE OF CORRECTION

| | | |
|---|---|---|
| PATENT NO. | : 8,053,444 B2 | Page 1 of 1 |
| APPLICATION NO. | : 12/011072 | |
| DATED | : November 8, 2011 | |
| INVENTOR(S) | : Sebastjan Reven, Igor Legen and Zdenka Jerala-Strukelj | |

It is certified that error appears in the above-identified patent and that said Letters Patent is hereby corrected as shown below:

Column 4, line 58, after 60°, "C." should be -- C --;

Column 4, line 59, "C." should be -- C --;

Column 5, line 61, after "cellulose" delete ".".

Column 6, TABLE 3, lines 35 - 54, in all instances, "C." should be -- C --;

Column 7, line 11, after 60°, "C." should be -- C --; and

Column 7, line 11, after 40°, "C." should be -- C --.

Signed and Sealed this
Fourteenth Day of February, 2012

David J. Kappos
*Director of the United States Patent and Trademark Office*